United States Patent
Knöpfle et al.

(10) Patent No.: US 9,034,020 B2
(45) Date of Patent: May 19, 2015

(54) IMPLANT FOR USE FOR ADJACENTLY ARRANGED BONE PLATES

(75) Inventors: Christian Knöpfle, Donaueschingen (DE); Regine Maurer, Freiburg (DE); Reinhard Rübecamp, Frankfurt (DE)

(73) Assignee: Stryker Leibinger GmbH & Co. KG (DE)

( * ) Notice: Subject to any disclaimer, the term of this patent is extended or adjusted under 35 U.S.C. 154(b) by 326 days.

(21) Appl. No.: 12/747,000

(22) PCT Filed: Dec. 14, 2007

(86) PCT No.: PCT/EP2007/011024
§ 371 (c)(1),
(2), (4) Date: Jul. 30, 2010

(87) PCT Pub. No.: WO2009/076978
PCT Pub. Date: Jun. 25, 2009

(65) Prior Publication Data
US 2010/0305619 A1    Dec. 2, 2010

(51) Int. Cl.
*A61B 17/68* (2006.01)

(52) U.S. Cl.
CPC .................................... *A61B 17/688* (2013.01)

(58) Field of Classification Search
CPC .............................. A61B 17/68; A61B 17/688
USPC ................... 606/300, 74, 75, 324, 326, 328, 606/902–906, 215, 70, 71; 623/17.17–17.19; 24/16 PB
See application file for complete search history.

(56) References Cited

U.S. PATENT DOCUMENTS

| 4,802,477 A | * | 2/1989 | Gabbay .......................... 606/74 |
| 5,350,399 A | * | 9/1994 | Erlebacher et al. ........... 606/213 |

(Continued)

FOREIGN PATENT DOCUMENTS

| DE | 9490219 U1 | 5/1996 |
| DE | 19952359 C1 | 3/2001 |

(Continued)

OTHER PUBLICATIONS

International Search Report, PCT/EP2007/011024, dated Aug. 27, 2008.

(Continued)

*Primary Examiner* — Christian Sevilla
*Assistant Examiner* — Eric S Gibson
(74) *Attorney, Agent, or Firm* — Lerner, David, Littenberg, Krumholz & Mentlik, LLP (57) ABSTRACT

An implant for use for adjacently arranged bone plates is described, having a first bearing part, a second bearing part and a coupling element for tension-proof coupling of the first bearing part to the second bearing part. The bearing parts are curved concavely and comprise a plurality of ribs, which extend radially outwards from a central portion of the respective bearing part. The upper bearing part comprises a main body and an insert connected thereto by means of at least one connecting element. The connecting element is supported against the coupling element with regard to movement into a release position. The upper bearing part additionally has a deflectable fixing element, which is supported against the upper bearing part in the event of movement of the upper bearing part away from the lower bearing part.

20 Claims, 5 Drawing Sheets (56) References Cited

U.S. PATENT DOCUMENTS

| | | | |
|---|---|---|---|
| 5,628,752 A | 5/1997 | Asnis et al. | |
| 5,976,141 A * | 11/1999 | Haag et al. | 606/292 |
| 6,532,631 B2 * | 3/2003 | Rohaly et al. | 24/16 PB |
| 6,755,834 B2 * | 6/2004 | Amis | 606/916 |
| 6,921,401 B2 * | 7/2005 | Lerch et al. | 606/324 |
| 7,060,067 B2 * | 6/2006 | Needham et al. | 606/86 B |
| 2002/0169455 A1 | 11/2002 | Bannerman et al. | |
| 2003/0036760 A1 * | 2/2003 | Yeh | 606/71 |
| 2003/0176890 A1 * | 9/2003 | Buckman et al. | 606/213 |
| 2004/0034352 A1 | 2/2004 | Needham et al. | |
| 2004/0116961 A1 * | 6/2004 | Nesper et al. | 606/216 |
| 2004/0127908 A1 * | 7/2004 | Roman et al. | 606/72 |
| 2004/0254579 A1 * | 12/2004 | Buhren et al. | 606/71 |

FOREIGN PATENT DOCUMENTS

| | | |
|---|---|---|
| EP | 1192909 A1 | 4/2002 |
| EP | 1808140 A1 | 7/2007 |
| EP | 1836981 A2 | 9/2007 |
| JP | 05220174 A | 8/1993 |
| JP | 2003180706 A | 7/2003 |
| JP | 2003235860 A | 8/2003 |
| WO | 2004028384 A1 | 4/2004 |

OTHER PUBLICATIONS

Codman & Shurtleff, Makers of Surgeons Instruments (1965).

* cited by examiner

IMPLANT FOR USE FOR ADJACENTLY ARRANGED BONE PLATES

CROSS REFERENCE TO RELATED APPLICATIONS

The present application is a national phase entry under 35 U.S.C. §371 of International Application No. PCT/EP2007/011024, filed Dec. 14, 2007, published in German, which is incorporated herein by reference.

FIELD OF THE INVENTION

The invention relates to an implant for example for fixing a bone flap to a cranial bone or for covering burr holes in the cranial bone. The implant has a first bearing part, a second bearing part and a coupling element for tension-proof coupling of the first bearing part with the second bearing part, in such a way that the bone flap and the cranial bone are arranged between the two bearing parts.

BACKGROUND OF THE INVENTION

Prior to removal of a brain tumor from under the cranial bone, the cranial bone has to be opened to provide access to the tumor. To this end, after the introduction of at least one burr hole into the cranial bone, a bone flap is sawed out of the cranial bone. After surgical removal of the tumor, the cranial bone has to be closed again. To this end, the previously sawed-out bone flap is generally refixed to the cranial bone by means of suitable implants. These implants are frequently also used to cover the burr holes.

Various implants are known for fixing a bone flap to a cranial bone and for covering burr holes. For instance, a brochure by Codman & Shurtleff from 1965 describes the "Todd Burr Hole Button." This implant comprises a first, disc-shaped bearing part with a shank projecting centrally from this bearing part. A second, likewise disc-shaped bearing part has a central opening and is threaded onto the shank in such a way that the latter extends through the opening.

Like the two bearing parts, the shank is made from a resilient plastics material and has an external diameter which is somewhat larger than the internal diameter of the opening in the second bearing part. A tensile force acting axially on the shank therefore brings about resilient extension of the shank and a reduction in the external shank diameter associated with the extension. As a consequence of this reduction in external diameter, the second bearing part may be threaded onto the shank and moved along the shank towards the first bearing part. If the tensile force acting on the shank is reduced, the external diameter of the shank increases again and ensures tension-proof coupling of the second bearing part with the shank and thus also with the first bearing part provided at the shank end.

A number of such implants are used to fix a bone flap to a cranial bone. Generally, a shank acting as coupling element for the two bearing parts is inserted into a gap between the bone flap and the cranial bone in such a way that the bone flap and the cranial bone are clamped between the two bearing parts.

The implant known from the Codman & Shurtleff brochure has not become established in practice. One of the reasons for this is the difficulty in handling the implant. For instance, the application of a tensile force to the shank and the displacement of a bearing part along the shank while the tensile force is maintained has proved extremely awkward. In addition the implant is not capable of maintaining high clamping forces reliably and in the long term.

JP 05 220 174 A discloses a further implant for fixing a bone flap to a cranial bone. The implant comprises a rectangular first bearing part with a strap projecting there-from and a rectangular second bearing part. The second bearing part has a central opening and is threaded onto the strap in such a way that the strap extends through the opening.

The implant strap is provided on one or both sides with teeth. The bearing part threaded onto the strap has up to two movable claws, that engage with the teeth provided on the strap. Both the teeth and the claws have a sawtooth-like profile, that provides less resistance to movement of the threaded-on bearing part towards the other bearing part than to movement in the opposite direction. This situation ensures tension-proof coupling of the two bearing parts, in such a way that the bone flap and the cranial bone may be clamped reliably therebetween.

BRIEF SUMMARY OF THE INVENTION

An embodiment of the present invention provides an implant for fixing two adjacently arranged bone plates that exhibit improved structural stability with regard to the tensile and clamping forces arising in the course of fixing the implant in place.

According to a first aspect of the present invention, an implant for use for adjacently arranged bone plates includes a first bearing part, a second bearing part, having at least one deflectable fixing element, and having a coupling element extending through the second bearing part and cooperating with the fixing element for tension-proof coupling of the first bearing part with the second bearing part, the coupling element being insertable into a gap between the bone plates in such a way that the two bone plates are arranged between the two bearing parts. A counter support for the at least one fixing element is provided on the second bearing part, which counter support is capable of supporting the fixing element in the event of movement of the second bearing part away from the first bearing part.

The fixing element may be supported in that the counter support limits deflection of the fixing element towards the first bearing part to a predetermined distance. According to a first variant, this distance amounts to no more than one or two millimeters, and the distance may even be limited to a few tenths of a millimeter. According to a second variant, the predetermined distance amounts to roughly zero. In other words, the fixing element may already rest against the counter support in its initial or normal position.

According to another aspect of the present invention, the second bearing part has at least two fixing elements opposite one another with regard to the coupling element, one counter support being provided for each fixing element. Thus, in the case of a strap-like coupling element two fixing elements may for example be provided, each fixing element cooperating with one of the two long sides of the strap. In the case of a connecting element of round or square cross-section, it is also possible to provide three, four or more fixing elements.

According to yet another aspect of the present invention, the at least one fixing element is deflectable in a direction parallel to a longitudinal axis of the coupling element. In this context the at least one fixing element may take the form of a tongue or claw. A tongue may be defined by two or more material incisions.

According to still yet another aspect of the present invention, the second bearing part has a main body and an insert attached thereto. The main body and the insert may consist of identical or indeed of different materials. Plastics and metals in particular are possible materials.

In the case of a multipart second bearing part the at least one fixing element may be formed in the insert, while the counter support is formed on the main body of the second bearing part. Alternatively, the fixing element may be provided on the main body and the counter support on the insert. In other embodiments, there may be a one-piece second bearing part, such that the fixing element and the counter support may be provided in one and the same component.

The coupling element may be provided with surface contouring. The at least one fixing element may cooperate with the surface contouring to achieve tension-proof fixing of the coupling element to the second bearing part. The surface contouring may comprise a series of teeth of any desired shape with a symmetrical or asymmetrical profile. According to one variant, the teeth have an asymmetrical (for example a sawtooth-like) profile, such that there is less resistance to movement of the second bearing part towards the first bearing part than to movement in the opposite direction.

According to a further aspect of the present invention, an implant for use for adjacently arranged bone plates, comprises a first bearing part, a second bearing part with a main body and with an insert attached to the main body, which insert comprises an opening, and a coupling element extending through the opening in the insert for tension-proof coupling of the first bearing part with the second bearing part, and the coupling element being insertable into a gap between the bone plates in such a way that the two bone plates are arranged between the two bearing parts. The insert is connected to the main body by means of at least one connecting element. The connecting element is supported against the coupling element with regard to movement into a release position.

The at least one connecting element may be provided on the main body and cooperate with the insert or be provided on the insert and then cooperate with the main body. Alternatively, the at least one connecting element may be provided on the main body and at least one further connecting element may be provided on the insert.

The insert and the main body may be connected together in different ways by means of the at least one connecting element. In this context interlocking and non-interlocking connections may be mentioned by way of example. According to one embodiment, the connecting element takes the form of a latching element. The latching element may comprise a snap-in hook, which is supported against the coupling element with regard to unlatching.

As already explained above, the insert may comprise at least one fixing element, by means of which the second bearing part may be fixed to the coupling element. The coupling element may comprise a strap; however coupling elements in the form of pins, cords or wires are also feasible. In addition, the two bearing parts may be coupled together by more than one coupling element. For example two or more parallel straps or pins may be provided.

According to a further aspect of the present invention, an implant for use for adjacently arranged bone plates has a first bearing part, a second bearing part and a coupling element extending through the second bearing part for tension-proof coupling of the first bearing part with the second bearing part, the coupling element being insertable into a gap between the bone plates in such a way that the two bone plates are arranged between the two bearing parts, and at least one of the two bearing parts being curved concavely towards the opposing bearing part. The at least one concavely curved bearing part comprises a plurality of ribs, which extend radially outwards from a central portion of this bearing part.

The individual ribs preferably begin roughly in the middle of the bearing part and may extend at least as far as into the vicinity of the outer circumference of the respective bearing part. The ribs do not all have to be of the same shape and length. Thus, some ribs may be shorter and other ribs longer.

According to one option between four and ten ribs are provided. The ribs may be uniformly or indeed non-uniformly spaced from one another. In each case two mutually adjacent ribs may in each case define a bearing part segment. If four or more such segments are provided, each segment will exhibit curvature substantially only in the radial direction. In other words, the curvature of a segment in the circumferential direction will be markedly less in such a case than the curvature thereof in the radial direction.

According to an embodiment, both bearing parts in each case exhibit concave curvature and ribs. According to another embodiment, only one of the two bearing parts, for example the second, is concavely curved and provided with ribs.

As already mentioned, various materials and material combinations are available for the implant. At least one of the two bearing parts may be made completely of plastics. It is however also feasible to make one bearing part, consisting of a main body with insert, of a metal/plastics combination. In such a case, the main body may be made of plastics and the insert of metal (or vice versa). Bio-absorbable plastics and/or thermoplastics such as polyether ether ketone (PEEK) or the variants and derivatives thereof are examples of possible plastics materials.

The first bearing part and the coupling element may be made in one piece or indeed as separate components. In the latter case, only after production thereof is the first bearing part connected loosely or rigidly to the coupling element.

BRIEF DESCRIPTION OF THE DRAWINGS

Further features and advantages of the invention are revealed by the following description of a preferred embodiment. In the Figures.

DETAILED DESCRIPTION

Figure 1:
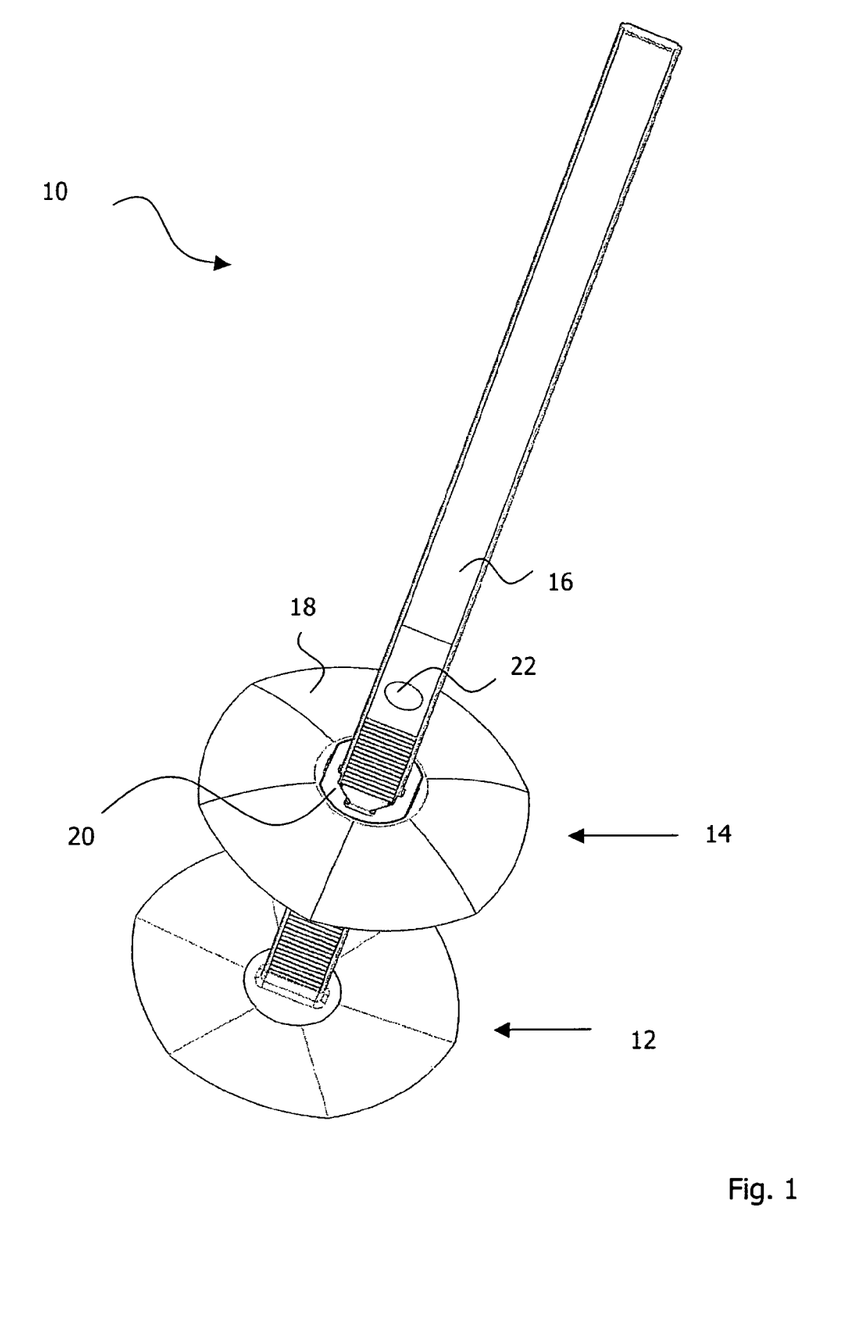
FIG. 1 is a perspective view of a fully assembled embodiment of an implant.

FIG. 1 shows a perspective view of an embodiment of an implant 10 for fixing two adjacently arranged bone plates. The implant is designed to be used to fix a bone flap to a cranial bone. The implant is also suitable however for use as a burr hole cover or as a sternum closure. For the latter use modifications generally known to a person skilled in the art may be undertaken. In this connection, reference should be made in general to document U.S. Pat. No. 4,802,477.

The implant 10 illustrated in FIG. 1 for fixing a bone flap to a cranial bone is made completely of plastics (for example PEEK). For the implant to be used in particular as a sternum closure, it may be desirable for the implant to display greater structural stability and therefore to be made at least in part of metal.

As illustrated in FIG. 1, the implant 10 comprises a first, lower bearing part 12 and a second, upper bearing part 14, which are coupled together in a tension-proof manner by means of a coupling element 16 in the form of a strap that is flexible with regard to bending movements. Tension is here understood to mean movement of the two bearing parts 12, 14 away from one another. As is generally known, to fix the bone flap to the cranial bone in a first step the strap 16 is arranged in a gap between the bone flap and the cranial bone. In a second step the upper bearing part 14 is then displaced either by hand or by means of an application tool along the strap 16 towards the lower bearing part 12 until the bone flap and the cranial bone are clamped securely between the two bearing parts 12, 14. As a rule between two and six such implants 10 are used, which are spaced uniformly from one another around the outer circumference of the bone flap and are optionally arranged in the region of burr holes.

Preferably, the lower bearing part 12 and the strap 16 form a one-piece first component, produced by injection moulding. The gate mark on the strap 16 is identified by reference numeral 22. The upper bearing part 14 threaded onto the strap 16 forms a second component consisting of a bearing part main body 18 and an insert 20 fastened in the main body 18.

Figure 2:
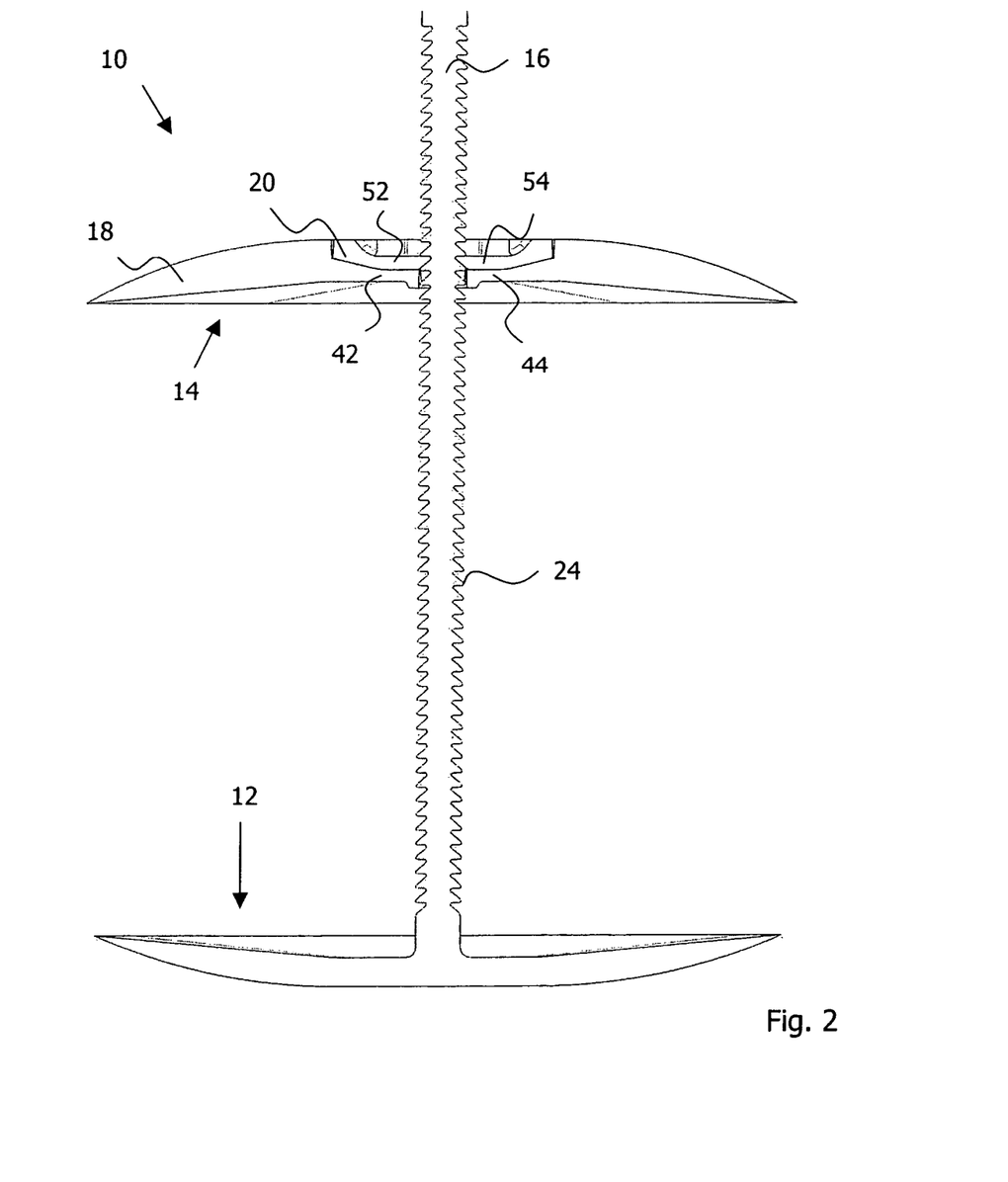
FIG. 2 is a sectional view of the fully assembled implant according to FIG. 1.

FIG. 2 shows a sectional representation of the lower part of the implant 10 in a plane perpendicular to the long side of the strap 16. FIG. 2 clearly shows the curved basic shape of the two bearing parts 12, 14. Each one of the two bearing parts 12, 14 is curved concavely towards the opposing bearing part 14, 12. The rigidity or deformability of the material (or the corresponding mixture of materials) used in practice for the bearing parts 12, 14 may be selected such that, in the course of fixing the implant 10 to the bone parts, the central portions of the bearing parts 12, 14 deform resiliently towards one another.

The side of the bearing part 12 facing the bearing part 14 and/or the surface of the bearing part 14 facing the bearing part 12 may be roughened. The peak-to-valley height may vary in the range between one and 100 µm. A peak-to-valley height of between five and 30 µm is preferred, for example an eroded structure according to VDI 3400 no. 45 (corresponding to a peak-to-valley height of 18 µm). Such roughening prevents the implant from slipping during the fixing process and also once implanted.

Figures 3, 4:
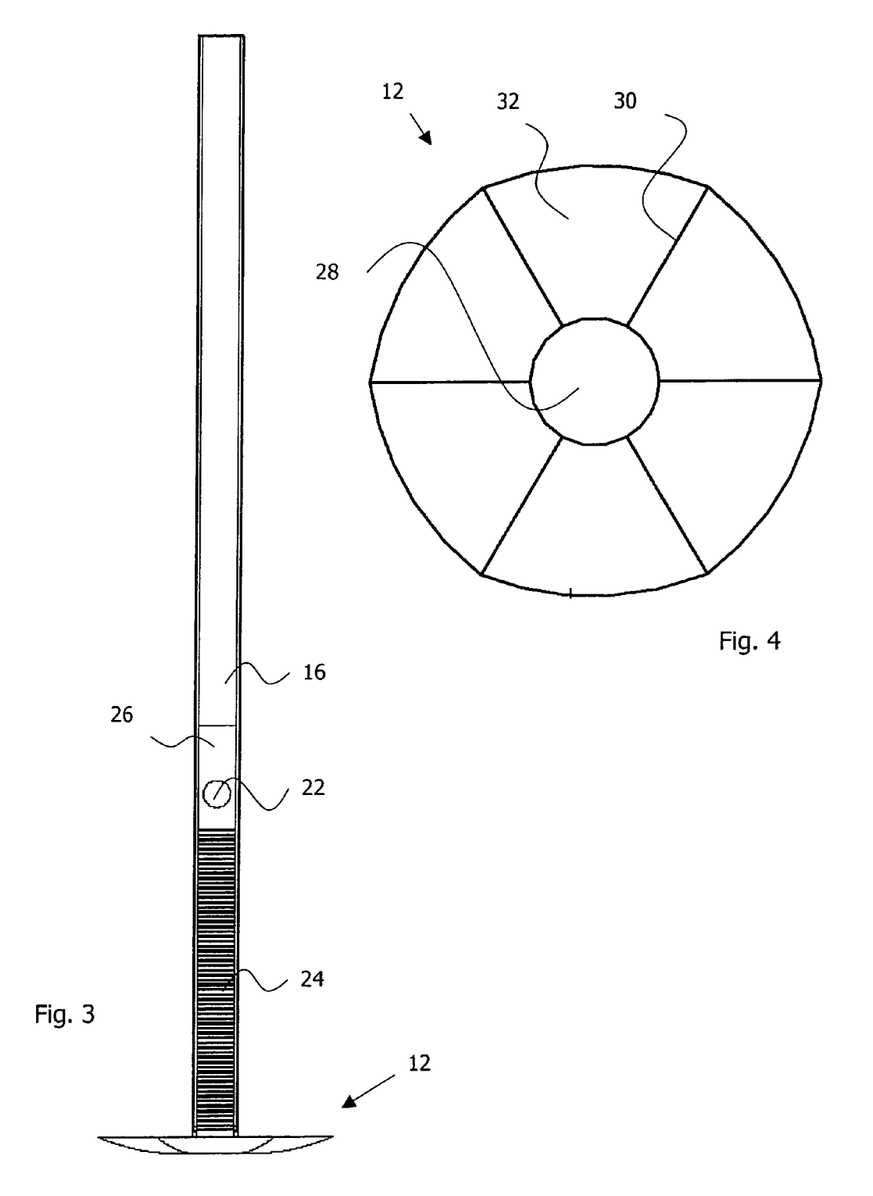
FIG. 3 is a side view of one component of the implant according to FIG. 1.
FIG. 4 is a view of the component of FIG. 3 from below.

FIG. 3 shows a side view of the one-piece component consisting of lower bearing part 12 and strap 16. It is easy to see that surface contouring of the strap 16 in the form of teeth 24 extends from the lower bearing part 12 over less than around a third of the total length of the strap 16. The remaining length of the strap 16 is substantially smooth or roughened and may serve as a point of application for an application tool.

Such application tools are generally known and are used to displace the upper bearing part 14 towards the lower bearing part 12. Some application tools are furthermore designed to cut off a portion of the strap 16 which projects above the upper bearing part 14.

The strap 16 is of a first thickness in the region of its smooth or roughened portion which increases gradually in a transitional region 26 to a second, somewhat greater thickness in the region of the teeth 24. This material thickness profile simplifies threading of the upper bearing part 14 onto the strap 16.

FIG. 4 shows the component of FIG. 2 (and in particular the lower bearing part 12) from below. The roughly circular outer contour of the lower bearing part 12 is apparent. The lower bearing part 12 has a central, circular portion 28 of maximum material thickness, which serves as an anchoring region for the strap 16 (which extends into the plane of the drawing in FIG. 3).

A total of six ribs 30 are provided starting from the central portion 28. The ribs 30 extend radially from the central portion 28 to the outer circumference of the lower bearing part 12. The ribs 30 have a reinforcing function with regard to the structural stability of the lower bearing part 12 for when the strap 16 is exposed to a tensile force and the bearing part 12 consequently moves into a bearing position with the bone plates to be coupled.

Due to the concave basic shape of the lower bearing part 12, each of the ribs 30 has a likewise concave curvature along its radial extent. Two adjacent ribs 30 in each case define a segment 32 with a curvature in the radial direction approaching the curvature of the ribs 30. The curvature of each segment 32 is on the other hand markedly less in the circumferential direction (i.e. perpendicular to the radial direction).

Figure 5:
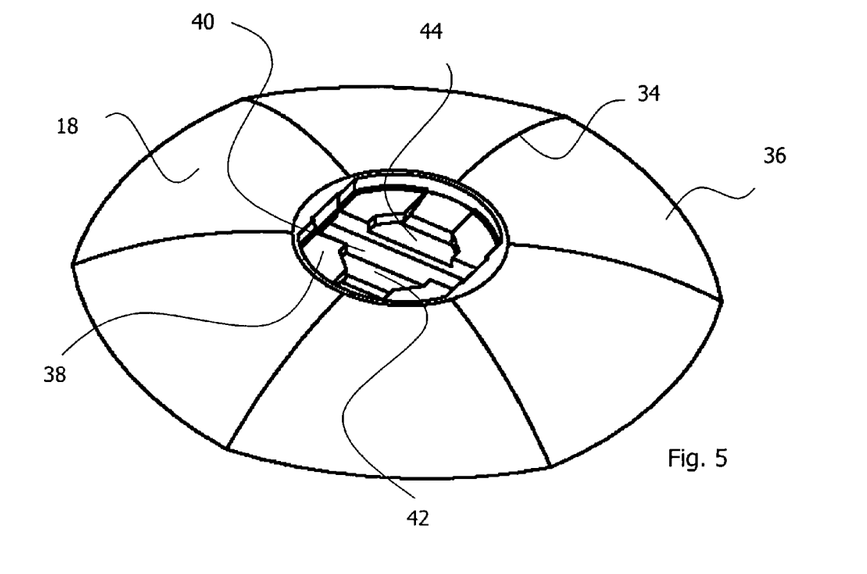
FIG. 5 is a perspective view of the main body of the upper bearing part of the implant according to FIG. 1.

FIG. 5 is a perspective view of the main body 18 of the upper bearing part. The shaping of the main body 18 of the upper bearing part 14 including the provision of a total of six ribs 34 with segments 36 arranged therebetween corresponds to the basic shape of the lower bearing part 12 explained above in relation to FIG. 4. For this reason the features of the main body 18 will not here be looked at in any greater detail.

FIG. 5 clearly reveals a recess 38 formed centrally in the main body 18 for accommodating the insert 20 shown in FIGS. 1 and 2. The insert 20 itself is not shown in FIG. 5.

The recess 38 leads into a rectangular opening 40 for accommodating the strap 16 and connecting elements provided on the insert. FIG. 5 shows that two sunken counter supports 42, 44 are provided in the recess 38, the function of which will be explained in greater detail below.

Figure 6:
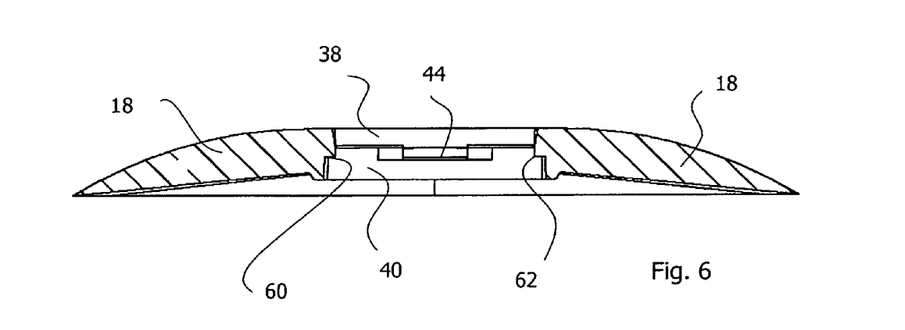
FIG. 6 is a sectional representation of the main body according to FIG. 5.

FIG. 6 shows a section through the main body 18 in a plane extending parallel to the longitudinal side of the opening 40 and containing the opening 40. The figure again clearly shows the concave shape of the main body 18 and the sunken counter support 44 provided within the recess 38.

Figure 7:
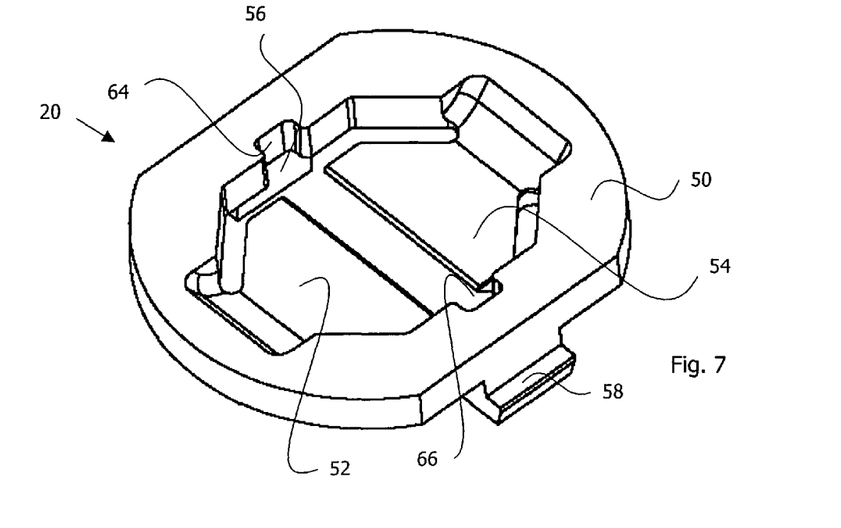
FIG. 7 is a perspective representation of an insert for fitting into the bearing part main body according to FIG. 5.

FIG. 7 shows a perspective view of the insert 20. The insert 20 has a main body 50, the outer contour of which corresponds to the inner contour of the recess 38 in the main body 18 according to FIG. 5. The insert 20 may therefore be accommodated in interlocking and non-rotatable manner in the recess 38.

Two opposing fixing elements in the form of deflectable tongues 52, 54 are provided on the main body 50. Each of the two tongues 52, 54 is resiliently deflectable upwards and downwards in a plane extending parallel to the strap 16. The mutually facing front ends of the tongues 52, 54 are at a distance from one another which is selected as a function of the thickness of the toothed strap portion such that the front ends of the tongues 52, 54, as shown in FIG. 2, may cooperate with the teeth 24 provided on the strap 16.

Figures 8, 9:
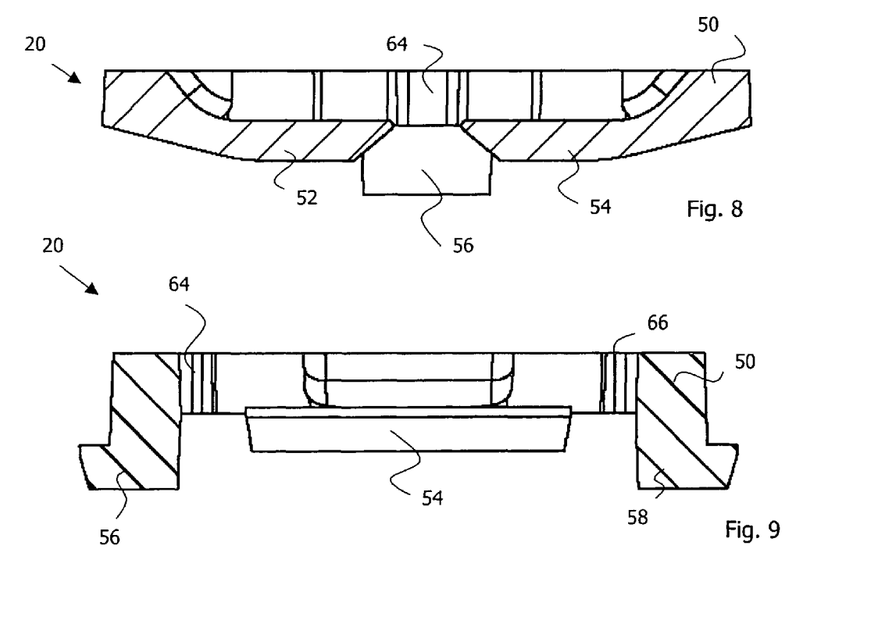
FIG. 8 is a first sectional representation of the insert according to FIG. 7.
FIG. 9 is a second sectional representation of the insert according to FIG. 7.

To achieve an interlocking connection between the tongues 52, 54 and the teeth 24 of the strap 16, the front ends of the tongues 52, 54, as apparent in the sectional representation according to FIG. 8, taper to a point. This shaping of the front ends of the tongues 52, 54 corresponds to the sawtooth profiling of the teeth 24. The front ends of the two tongues 52, 54 may therefore be accommodated interlockingly between two adjacent teeth 24. Due to the asymmetric profiling of each of the teeth 24, interaction between the tongues 52, 54 of the insert 20 and the teeth 24 of the strap 16 proceeds such that there is less resistance to displacement of the upper bearing part 14 towards the lower bearing part 12 than to displacement of the upper bearing part 14 in the opposite direction.

In order further to increase the resistance which the interaction between the tongues 52, 54 and the teeth 24 provides to movement of the upper bearing part 14 away from the lower bearing part 12 (and thus the maximum achievable clamping force), the counter supports 42, 44 explained above in relation to FIG. 5 and provided on the main body 18 of the upper bearing part 14 come into play. As shown in FIG. 2, in the initial state the two tongues 52, 54 rest flat on the two counter supports 42, 44. The counter supports 42, 44 therefore support the tongues in the event of movement of the upper bearing part 14 away from the lower bearing part 12. This support opposes downward deflection of the tongues 52, 54 and the associated upward mobility of the upper bearing part 14 in FIG. 2, since the front tips of the tongues 52, 54 cannot be released from the teeth 24 (or only if considerable force is expended). The supporting action of the counter supports 42, 44 increases markedly overall the maximum clamping force achievable with the implant 10 over conventional implants and in particular that of plastics-based implants.

The support of the tongues 52, 54 on the counter supports 42, 44 in the event of the introduction of a force which urges the two bearing parts 12, 14 away from one another naturally greatly increases the counterforces introduced into the insert 20. These counterforces are directed towards detaching the insert 20 from the main body 18. For this reason, efficient anchoring of the insert 20 in the main body 18 is indispensable.

As is shown in FIG. 7, the main body 50 of the insert 20 comprises two connecting elements formed as latching elements 56, 58 for fastening the insert 20 to the main body 18 of the upper bearing part 14. The two latching elements 56, 58 are of hook-shaped construction and provided on opposing sides of the main body 50 of the insert 20 (sectional representation according to FIG. 9).

The insert 20 is then inserted into the main body 18 of the upper bearing part 14 in such a way that the latching elements 56, 58 engage behind the main body 18 of the upper bearing part 14 in the region of the short sides of the opening 40. With reference to the sectional representation of the main body 18 according to FIG. 6, the hook shapes of the latching elements 56, 58 thus engage behind the main body 18 in the region of steps of the main body 18 provided with reference numerals 60 and 62.

The clamping forces which have to be applied to fix a bone plate to a cranial bone may then become so significant that the resultant counterforces bring with them the risk of unlatching of the latching elements 56, 58. To counter this risk, the latching elements 56, 58 are supported against the strap 16 with regard to movement into a release position (i.e. in FIG. 9 towards the tongue 54). To this end the main body 50 of the insert 20 shown in FIG. 7 comprises guide channels 64, 66 in regions adjoining the backs of the latching elements 56, 58 for guiding the strap 16 along its short sides. This situation is also illustrated in FIG. 1.

As a result the latching elements 56, 58 are supported against the short sides of the strap 16 in the event of movement in the direction of a release position (i.e. in FIG. 9 towards the tongue 54). This support opposes further movement of the latching elements 56, 58 towards their release position, such that the insert 20 remains reliably anchored in the main body 18 of the upper bearing part 14. The consequent advantage of achieving extremely high clamping forces is reliably underpinned by the above-described shaping of the two bearing parts 12, 14 with reinforcing ribs 30, 34.

Although the reinforcing ribs 30, 34, the counter supports 42, 44 and the support of the latching elements 56, 58 in combination bring about particularly advantageous effects, these technical features may also be used mutually independently, in order to achieve individually the technical effects associated with the respective feature. It should additionally be pointed out that the technical features have a particularly advantageous effect when combined with plastics material, but the implant may also be made partially or completely of metal while exploiting the same technical effects.

The invention claimed is:

1. An implant for use for adjacently arranged bone plates, having:
 a first bearing part;
 a second bearing part, which comprises a main body and an insert fastened in a recess of the main body such that an outer surface of the insert lies flush with an outer surface of the main body, wherein at least one deflectable fixing element is provided on the insert with an elongated body extending between a first end attached to the insert and a second end having a tip; and
 a coupling element extending through the second bearing part and cooperating with the fixing element for tension-proof coupling of the first bearing part with the second bearing part, the coupling element being insertable into a gap between the bone plates in such a way that the two bone plates are arranged between the two bearing parts,
 wherein a counter support for the fixing element is provided on the main body to limit deflection of the fixing element in the event of movement of the second bearing part away from the first bearing part, the counter support having an abutment surface that continuously supports the elongated body of the deflectable fixing element.

2. The implant according to claim 1, wherein the counter support limits deflection of the fixing element towards the first bearing part to a predetermined distance.

3. The implant according to claim 1, wherein the second bearing part has at least two fixing elements opposite one another with regard to the coupling element, and wherein a counter support is provided for each of the fixing elements.

4. The implant according to claim 1, wherein the at least one fixing element takes the form of a tongue or claw.

5. The implant according to claim 1, wherein the coupling element comprises surface contouring and the at least one fixing element cooperates with the surface contouring for tension-proof fixing of the coupling element to the second bearing part.

6. The implant according to claim 5, wherein the surface contouring takes the form of a series of teeth.

7. The implant according to claim 6, wherein the teeth have an asymmetrical profile, such that there is less resistance to movement of the second bearing part towards the first bearing part than to movement in the opposite direction.

8. An implant for use for adjacently arranged bone plates, having:
 a first bearing part;
 a second bearing part with a main body and an insert fastened in a recess of the main body such that an outer surface of the insert lies flush within the main body, wherein the insert comprises an opening with at least one channel; and
 a coupling element with at least one key extending through the opening in the insert for tension-proof coupling of the first bearing part with the second bearing part, the coupling element being insertable into a gap between the bone plates in such a way that the two bone plates are arranged between the two bearing parts, wherein the insert is latched to the main body by at least one latching element having an interior surface supported against the coupling element to oppose movement of the latching element into a release position, and wherein the at least one key of the coupling element is adjacent the interior surface of the at least one latching element when the coupling element is inserted into the opening.

9. The implant according to claim 8, wherein the at least one connecting element is provided on the main body.

10. The implant according to claim 8, wherein the at least one connecting element is provided on the insert.

11. The implant according to claim 10, wherein the insert is attached to the main body by means of two connecting elements, which are supported against opposing sides of the coupling element with regard to movement into a release position.

12. The implant according to claim 8, wherein the insert bears at least one fixing element by means of which the second bearing part may be fixed to the coupling element.

13. An implant for use for adjacently arranged bone plates, having:
    a first bearing part;
    a second bearing part with a recess;
    an insert with an opening, the insert being adapted to interlock within the recess of the second bearing part in a non-rotatable manner by at least one latching element; and
    a coupling element extending through the second bearing part and the opening in the insert for tension-proof coupling of the first bearing part with the second bearing part, the coupling element being insertable into a gap between the bone plates in such a way that the two bone plates are arranged between the two bearing parts,
    wherein each of the two bearing parts being curved concavely towards the opposing bearing part, and
    wherein each of the first and second concavely curved bearing part has an outer surface with a plurality of ribs extending radially outwards from a central portion of the bearing part.

14. The implant according to claim 13, wherein between four and ten ribs are provided.

15. The implant according to claim 13, wherein two adjacent ribs in each case define a bearing part segment and each segment exhibits curvature in the radial direction.

16. The implant according to claim 13, wherein at least one of the two bearing parts is made of plastics.

17. The implant according to claim 16, wherein the implant is made at least from PEEK.

18. The implant according to claim 13, wherein the first bearing part is made in one piece with the coupling element.

19. The implant according to claim 18, wherein the first bearing part is roughened on its surface facing the second bearing part and/or the second bearing part is roughened on its surface facing the first bearing part.

20. The implant according to claim 13, wherein the insert is fastened to the second bearing part adjacent the opening so as to lie flush within the second bearing part, and wherein at least one deflectable fixing element is provided on the insert.

* * * * *